United States Patent

Kuhnt et al.

[11] Patent Number: 5,412,149
[45] Date of Patent: May 2, 1995

[54] PROCESS FOR THE PREPARATION OF 2-OXIMINOACETIC ACID DERIVATIVES

[75] Inventors: Dietmar Kuhnt, Leverkusen; Herbert Gayer, Monheim; Peter Gerdes, Aachen, all of Germany

[73] Assignee: Bayer Aktiengesellschaft, Leverkusen, Germany

[21] Appl. No.: 239,196

[22] Filed: May 6, 1994

[30] Foreign Application Priority Data

May 14, 1993 [DE] Germany .......... 43 06 187.1
Jun. 21, 1993 [DE] Germany .......... 43 20 499.6

[51] Int. Cl.$^6$ .................. C07C 229/10; C07C 249/08
[52] U.S. Cl. ........................ 560/35; 564/147; 546/290; 549/62; 549/416
[58] Field of Search ............. 560/35; 564/147; 546/290; 549/62, 416

[56] References Cited

FOREIGN PATENT DOCUMENTS

| | | |
|---|---|---|
| 253213 | 1/1988 | European Pat. Off. |
| 254426 | 1/1988 | European Pat. Off. |
| 385357 | 5/1990 | European Pat. Off. |
| 398692 | 11/1990 | European Pat. Off. |
| 468775 | 1/1992 | European Pat. Off. |
| 493711 | 7/1992 | European Pat. Off. |
| 2249092 | 4/1992 | United Kingdom. |

Primary Examiner—José G. Dees
Assistant Examiner—Joseph M. Conrad
Attorney, Agent, or Firm—Sprung Horn Kramer & Woods

[57] ABSTRACT

A new process and new intermediates are described for the preparation of 2-oximinoactic acid derivatives of the formula (I)

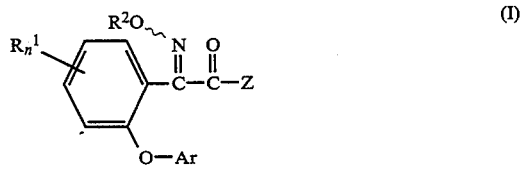

in which $R^1$, $R^2$, n, Z and Ar have the meaning given in the description and which are used as pesticides.

7 Claims, No Drawings

PROCESS FOR THE PREPARATION OF 2-OXIMINOACETIC ACID DERIVATIVES

The invention relates to a new process and to new intermediates for the preparation of 2-oximinoacetic acid derivatives, which are used as pesticides.

It is known that fungitidal 2-methoximino-2-phenylacetic acid derivatives are obtained by a number of generally multi-stage synthesis routes, in which in general the corresponding 2-oxo-2-phenylacetic acid derivatives occur as the central intermediates (cf. e.g. EP 398 692 and EP 468 775). The disadvantage of all these synthesis routes consists in the fact that these 2-oxo-2-phenylacetic acid derivatives are prepared by reaction with organometallic compounds (e.g. n-butyllithium), a method which is complicated to carry out industrially. In addition, the yields of the processes known to date are generally unsatisfactory.

It has been found that fungitidal 2-oximinoacetic acid derivatives of the general formula (I)

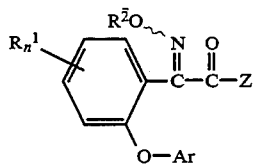

in which
  $R^1$ represents alkyl or alkoxy,
  $R^2$ represents alkyl,
  Ar represents optionally substituted aryl or heteroaryl,
  Z represents a radical of the formula $-O-R^3$ or $-NR^4R^5$ and
  n represents a number 0, 1, 2, 3 or 4, where
  $R^3$ represents alkyl and
  $R^4$ and $R^5$, independently of one another, each represent hydrogen, alkyl, halogenoalkyl or alkoxy,
are obtained if 2-oxo-2-phenyl-acetic acid derivatives of the formula (II)

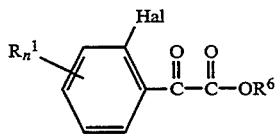

in which
  Hal represents halogen,
  $R^6$ represents hydrogen or alkyl and
  $R^1$ and n have the meaning given above,
are initially reacted, in a 1st stage, with alcohols of the formula (IIIa)

in which
  $R^7$ represents alkyl,
or with diols of the formula (IIIb),

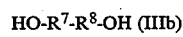

in which
  $R^7$ and $R^8$ together represent a divalent alkanediyl radical, optionally in the presence of a diluent and optionally in the presence of a reaction auxiliary, and, in a subsequent 2nd stage, the 2-aryl-2,2-dialkoxy-acetic acid derivatives of the formula (IVa)

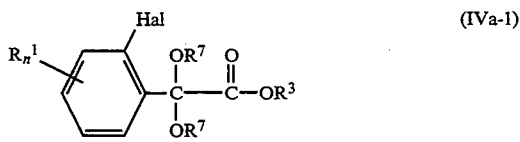

and

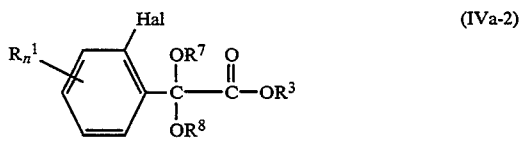

in which
  $R^1$, $R^3$, $R^7$, $R^8$, Hal and n have the meaning given above, which compounds are thus obtainable, are reacted with hydroxy compounds of the formula (V)

in which
  Ar has the meaning given above,
optionally in the presence of a diluent and optionally in the presence of a reaction auxiliary, and subsequently the 2-aryl-2,2-dialkoxy-acetic acid derivatives of the formula (VIa)

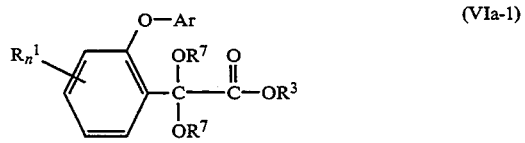

and

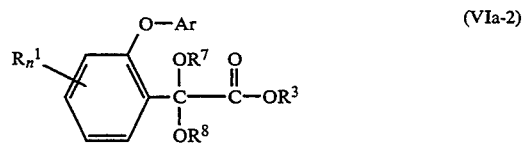

in which
  $R^1$, $R^3$, $R^7$, $R^8$, Ar and n have the meaning given above,
which compounds are thus obtainable, are reacted in a subsequent 3rd stage with hydroxylamine derivatives of the formula (VII)

in which
  $R^2$ has the meaning Given above
or with their hydrohalide salts, optionally in the presence of a diluent and optionally in the presence of a reaction auxiliary, to give the 2-oximinoacetic acid derivatives of the formula (Ia)

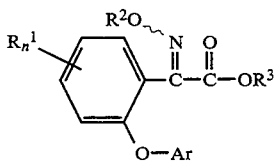
(Ia)

in which
R¹, R², R³, Ar and n have the meaning given above.

In this procedure, it is optionally possible for either the 2-aryl-2,2-dialkoxy-acetic acid derivatives of the formula (IVa) which are obtainable in the first stage or the 2-aryl-2,2-dialkoxy-acetic acid derivatives of the formula (VIa) which are obtainable in the second stage or the 2-oximinoacetic acid derivatives of the formula (Ia) which are obtainable in the third stage to be reacted, in an interposed reaction or in a subsequent reaction, in each case with amines of the formula (VIII)

(VIII)

in which
R⁵ and R⁶ have the meaning given above, optionally in the presence of a diluent and optionally in the presence of a reaction auxiliary. In this case, the starting compounds employed for the 2nd or 3rd stage of the preparation process according to the invention are the respective to correspond amides of the formulae (IVb)

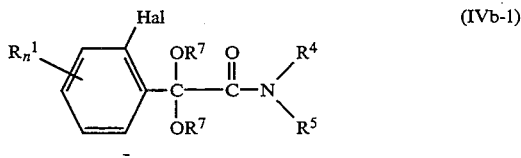
(IVb-1)

and

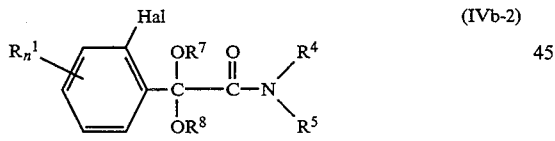
(IVb-2)

in which
R¹, R⁴, R⁵, R⁷, R⁸, Hal and n have the meaning given above,
or, respectively, (VIb)

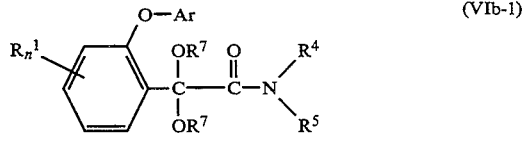
(VIb-1)

and

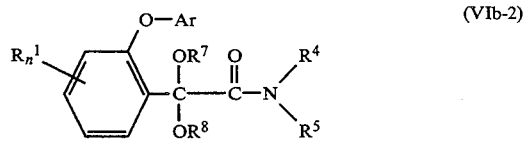
(VIb-2)

in which
R¹, R⁴, R⁵, R⁷, R⁸, Ar and n have the meaning given above.

Surprisingly, when the process according to the invention is carried out, the desired fungicidally active 2-oximinoacetic acid derivatives of the formula (I) are obtained in a smooth reaction and in a better yield over all the stages than by the processes known from the prior art.

Moreover, it is also to be regarded as particularly surprising that the reaction, in the 2nd stage of the process according to the invention, of the 2-halogeno group in the phenyl moiety of the intermediates of the formulae (IVa) and (IVb) with phenols of the formula (V), in the presence of a ketal structure in the position adjacent to the phenyl ring, proceeds in a smooth reaction, since the comparable reaction of corresponding 2-oxo-2-phenyl-acetic acid derivatives or corresponding 2-alkoximino-2-phenyl-acetic acid derivatives with phenols of the formula (V) leads to extensive decomposition of the starting products, without any appreciable amounts of the desired end product being obtained.

A particular advantage of the process according to the invention in this context is that it is possible to use easily accessible precursors and to avoid the use of organometallic compounds, for example butyllithium, which are difficult to handle on a large industrial scale.

A general definition of the 2-oximinoacetic acid derivatives which can be prepared in accordance with the invention is given by the formula (I). Compounds of the formula (I) which it is preferably possible to prepare are those in which R¹ represents straight-chain or branched alkyl having from 1 to 6 carbon atoms or represents straight-chain or branched alkoxy having from 1 to 6 carbon atoms, R² represents straight-chain or branched alkyl having from 1 to 6 carbon atoms.

Ar represents aryl having from 6 to 10 carbon atoms or heteroaryl having from 2 to 9 carbon atoms and from 1 to 4 identical or different hetero atoms—in particular nitrogen, oxygen and/or sulphur—each of which are optionally substituted once or more than once by identical or different substituents, possible substituents in each case being:

Halogen, cyano, nitro, in each case straight-chain or branched alkyl, alkoxy or alkylthio having in each case from 1 to 6 carbon atoms, in each case straight-chain or branched alkenyl or alkenyloxy having in each case from 2 to 6 carbon atoms, in each case straight-chain or branched alkinyl or alkinyloxy having in each case from 2 to 6 carbon atoms, in each case straight-chain or branched halogenoalkyl, halogenoalkoxy, halogenoalkylthio having in each case from 1 to 6 carbon atoms and from 1 to 13 identical or different halogen atoms, in each case straight-chain or branched halogenoalkenyl or halogenoalkenyloxy having in each case from 2 to 6 carbon atoms and from 1 to 13 identical or different halogen atoms, in each case straightchain or branched halogenoalkinyl or halogenoalkinyloxy having in each case from 2 to 6 carbon atoms and from 1 to 13 identical or different halogen atoms, in each case straight-chain or branched alkoxycarbonyl, hydroximinoalkyl or alkoximinoalkyl having in each case from 1 to 6 carbon atoms in the individual alkyl moieties, divalent dioxyalkylene having from 1 to 5 carbon atoms which is optionally substituted once or more than once by identical or different substituents comprising halogen and/or straight-chain or branched alkyl having from 1 to 6 carbon atoms and/or straightchain or branched halogenoalkyl having from 1 to 6 carbon atoms and from 1 to 13 identical or different halogen atoms—in particular fluorine, chlorine, bromine and/or iodine—or phenyl, phenoxy, benzyl, benzyloxy, phenylethyl or phenylethyloxy each of which is optionally substituted in the phenyl moiety once or more than once by identical or different substituents comprising halogen and/or straightchain or branched alkyl having from 1 to 4 carbon atoms and/or straight-chain or branched halogenoalkyl having from 1 to 4 carbon atoms and from 1 to 9 identical or different halogen atoms and/or straight-chain or branched alkoxy having from 1 to 4 carbon atoms and/or straight-chain or branched halogenoalkoxy having from 1 to 4 carbon atoms and 1 to 9 identical or different halogen atoms, z represents a radical of the formula $-O-R^3$ or $-NR^4R^5$ and n represents a number 0, 1, 2, 3 or 4, where $R^3$ represents straight-chain or branched alkyl having from 1 to 6 carbon atoms and $R^4$ and $R^5$, independently of one another, each represent hydrogen, straight-chain or branched alkyl having from 1 to 8 carbon atoms, straight-chain or branched halogenoalkyl having from 1 to 6 carbon atoms and from 1 to 13 identical or different halogen atoms, or represent straight-chain or branched alkoxy having from 1 to 8 carbon atoms.

Compounds of the formula (I) which it is particularly preferably possible to prepare are those in which $R^1$ represents straight-chain or branched alkyl having from 1 to 4 carbon atoms or represents straight-chain or branched alkoxy having from 1 to 4 carbon atoms, $R^2$ represents straight-chain or branched alkyl having from 1 to 4 carbon atoms, Ar represents aryl having 6 or 10 carbon atoms or heteroaryl having from 2 to 9 carbon atoms and from 1 to 3 identical or different hetero atoms—in particular nitrogen, oxygen and/or sulphur—each of which is optionally substituted once to five times by identical or different substituents, possible substituents in each case being:

Halogen, cyano, nitro, in each case straight-chain or branched alkyl, alkoxy or alkylthio having in each case from 1 to 4 carbon atoms, in each case straight-chain or branched alkenyl or alkenyloxy having in each case from 2 to 5 carbon atoms, in each case straight-chain or branched alkinyl or alkinyloxy having in each case from 2 to 5 carbon atoms, in each case straight-chain or branched halogenoalkyl, halogenoalkoxy or halogenoalkylthio having in each case from 1 to 4 carbon atoms and from 1 to 9 identical or different halogen atoms, in each case straight-chain or branched halogenoalkenyl or halogenoalkenyloxy having in each case from 2 to 5 carbon atoms and from 1 to 5 identical or different halogen atoms, in each case straight-chain or branched halogenoalkinyl or halogenoalkinyloxy having in each case from 2 to 5 carbon atoms and from 1 to 5 identical or different halogen atoms, in each case straight-chain or branched alkoxycarbonyl, hydroximinoalkyl or alkoximinoalkyl having in each case from 1 to 4 carbon atoms in the individual alkyl moieties, divalent dioxyalkylene having from 1 to 3 carbon atoms which is optionally substituted once to four times by identical or different substituents comprising halogen and/or straight-chain or branched alkyl having from 1 to 4 carbon atoms and/or straight-chain or branched halogenoalkyl having from 1 to 4 carbon atoms and from 1 to 9 identical or different halogen atoms—in particular fluorine, chlorine and/or bromine—or phenyl, phenoxy, benzyl, benzyloxy, phenylethyl or phenylethyloxy each of which is optionally substituted in the phenyl moiety once to five times by identical or different substituents comprising halogen and/or straight-chain or branched alkyl having from 1 to 4 carbon atoms and/or straight-chain or branched halogenoalkyl having from 1 to 3 carbon atoms and from 1 to 7 identical or different halogen atoms and/or straight-chain or branched alkoxy having from 1 to 4 carbon atoms and/or straight-chain or branched halogenoalkoxy having from 1 to 3 carbon atoms and 1 to 7 identical or different halogen atoms, Z represents a radical of the formula $-O-R^3$ or $NR^4R^5$ and n represents a number 0, 1, 2 or 3, where $R^3$ represents straight-chain or branched alkyl having from 1 to 4 carbon atoms and $R^4$ and $R^5$, independently of one another, each represent hydrogen, straight-chain or branched alkyl having from 1 to 6 carbon atoms, straight-chain or branched halogenoalkyl having from 1 to 4 carbon atoms and from 1 to 9 identical or different halogen atoms, or represent straight-chain or branched alkoxy having from 1 to 6 carbon atoms.

Compounds of the formula (I) which it is very particularly preferably possible to prepare are those in which $R^1$ represents methyl, methoxy, ethyl or ethoxy, $R^2$ represents methyl or ethyl, Ar represents phenyl which is optionally substituted once to three times by identical or different substituents, possible substituents in each case being:

Fluorine, chlorine, bromine, cyano, nitro, methyl, ethyl, n- or i-propyl, n-, i-, s- or t-butyl, methoxy, ethoxy, n- or i-propoxy, n-, i-, s- or t-butoxy, methylthio, ethylthio, allyl, butenyl, allyloxy, butenyloxy, trifluoromethyl, trifluoromethoxy, difluoromethoxy, trifluoromethylthio, difluorochloromethylthio, methoxycarbonyl, ethoxycarbonyl, hydroximinomethyl, hydroximinoethyl, methoximinomethyl, methoximinoethyl, ethoximinomethyl, ethoximinoethyl, divalent dioxymethylene or dioxyethylene each of which is optionally substituted once to four times by identical or different substituents comprising fluorine, chlorine, bromine, methyl, ethyl and/or trichloromethyl, or phenyl, phenoxy, benzyl or benzyloxy each of which is optionally substituted once to three times by identical or different substituents comprising fluorine, chlorine, bromine, methyl, ethyl, methoxy, ethoxy, trifluoromethyl and/or trifluoromethoxy, Z represents a radical of the formula $-O-R^3$ or $-NR^4R^5$ and n represents a number 0.1, or 2, where $R^3$ represents methyl or ethyl and $R^4$ and $R^5$, independently of one another, each represent hydrogen, straight-chain or branched alkyl having from 1 to 4 carbon atoms, halogenoalkyl having from 1 to 4 carbon atoms and from 1 to 5 identical or different halogen atoms, or represent straight-chain or branched alkoxy having from 1 to 4 carbon atoms.

Using, for example, methyl 2-chlorophenylglyoxylate and methanol as starting substances, the sequence of reaction of the process according to the invention can be represented by the following formula scheme:

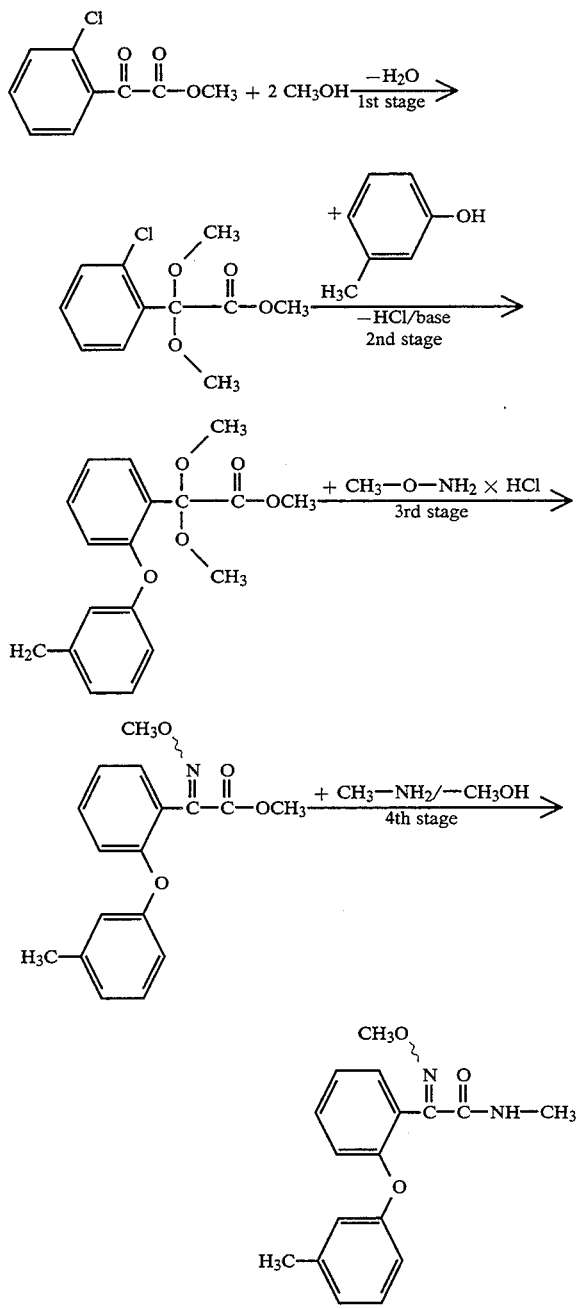

A general definition of the 2-oxo-2-phenyl-acetic acid derivatives which are required in the first stage as starting compounds for carrying out the process according to the invention is given by the formula (II). In this formula (II), $R^1$ and n preferably represent those radicals and indices which have already been mentioned as preferred for these substituents and this index in connection with the description of the compounds of the formula (I) which can be prepared in accordance with the invention. $R^6$ preferably represents hydrogen or represents straight-chain or branched alkyl having from 1 to 4 carbon atoms, and in particular represents hydrogen, methyl or ethyl. Hal preferably represents fluorine, chlorine, bromine or iodine, especially chlorine or bromine.

2-Oxo-2-phenyl-acetic acid derivatives of the formula (II) are known or are obtainable by analogy with known processes (cf. e.g. FR 15 56 822; J. Sci. Soc. Thailand 8, 215–223 [1982]).

A general definition of the alcohols or diols also required as starting substances for the process according to the invention in the first stage is given by the formulae (IIIa) and (IIIb), respectively. In these formulae (IIIa) and (IIIb), $R^7$ and $R^8$ preferably each represent straight-chain or branched alkyl having from 1 to 6, in particular from 1 to 4, carbon atoms or together represent a divatent alkanediyl radical having from 1 to 6 carbon atoms.

The alcohols or diols of the formulae (IIIa) and (IIIb) are commonly known compounds of organic chemistry.

A general definition of the hydroxy compounds also required as starting substances for carrying out the process according to the invention in the second stage is given by the formula (V). In this formula (V), Ar preferably represents those radicals which have already been mentioned as preferred for these substituents in connection with the description of the compounds of the formula (I) which can be prepared in accordance with the invention.

The hydroxy compounds of the formula (V) are likewise commonly known compounds of organic chemistry.

A general definition of the hydroxylamine derivatives also required as starting substances for carrying out the process according to the invention in the third stage is given by the formula (VII). In this formula (VII), $R^2$ preferably represents those radicals which have already been mentioned as being preferred for these substituents in connection with the description of the compounds of the formula (I) which can be prepared in accordance with the invention. Particularly suitable hydrohalides thereof are the hydrochlorides and hydrobromides.

The hydroxylamine derivatives of the formula (VII) and their hydrohalides are likewise commonly known compounds of organic chemistry.

A general definition of the amines which may also be required as starting substances for carrying out the process according to the invention is given by the formula (VIII). In this formula (VIII), $R^4$ and $R^5$ preferably represent those radicals which have already been mentioned as being preferred for these substituents in connection with the description of the compounds of the formula (I) which can be prepared in accordance with the invention.

The amines of the formula (VIII) are likewise commonly known compounds of organic chemistry.

The 2-aryl-2,2-dialkoxy-acetic acid derivatives of the formula (IX)

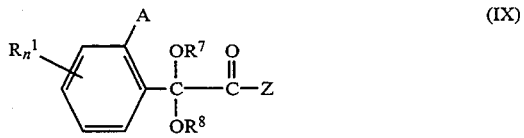

in which $R^1$ represents alkyl or alkoxy, $R^7$ and $R^8$ are either identical and in each case represent alkyl, or together represent a divalent alkanediyl radical, A represents halogen or represents optionally substituted aryloxy or heteroaryloxy, represents a radical of the formula -O-$R^3$ or -$NR^4R^5$ and n represents a number 0, 1, 2, 3 or 4, where $R^3$ represents alkyl and $R^4$ and $R^5$, independently of one another, each represent hydrogen, alkyl, halogenoalkyl or alkoxy which occur as intermediates when carrying out the process according to the invention correspond to the compounds of the formulae (IV) and (VI), and were not previously known and are likewise a subject of the invention.

Preferred compounds of the formula (IX) are those in which $R^1$ represents straight-chain or branched alkyl having from 1 to 6 carbon atoms or represents straight-chain or branched alkoxy having from 1 to 6 carbon atoms, $R^7$ and $R^8$ are either identical and represent straight-chain or branched alkyl having from 1 to 6 carbon atoms, or together represent a divalent alkanediyl radical having from 1 to 6 carbon atoms, A represents fluorine, chlorine, bromine or iodine or represents aryloxy having from 6 to 10 carbon atoms or heteroaryloxy having from 2 to 9 carbon atoms and from 1 to 4 identical or different hetero atoms—in particular nitrogen, oxygen and/or sulphur—each of which is optionally substituted once or more than once by identical or different substituents, possible substituents in each case being:

Halogen, cyano, nitro, in each case straight-chain or branched alkyl, alkoxy or alkylthio having in each case from 1 to 6 carbon atoms, in each case straight-chain or branched alkenyl or alkenyloxy having in each case from 2 to 6 carbon atoms, in each case straight-chain or branched alkinyl or alkinyloxy having in each case from 2 to 6 carbon atoms, in each case straight-chain or branched halogenoalkyl, halogenoalkoxy or halogenoalkylthio having in each case from 1 to 6 carbon atoms and from 1 to 13 identical or different halogen atoms, in each case straight-chain or branched halogeno-alkenyl or halogenoalkenyloxy having in each case from 2 to 6 carbon atoms and from 1 to 13 identical or different halogen atoms, in each case straight-chain or branched halogenoalkinyl or halogeno-alkinyloxy having in each case from 2 to 6 carbon atoms and from 1 to 13 identical or different halogen atoms, in each case straight-chain or branched alkoxycarbonyl, hydroximinoalkyl or alkoximinoalkyl having in each case from 1 to 6 carbon atoms in the individual alkyl moieties, divalent dioxyalkylene having from 1 to 5 carbon atoms which is optionally substituted once or more than once by identical or different substituents comprising halogen and/or straight-chain or branched alkyl having from 1 to 6 carbon atoms and/or straightchain or branched halogenoalkyl having from 1 to 6 carbon atoms and from 1 to 13 identical or different halogen atoms—in particular fluorine, chlorine, bromine and/or iodine—or phenyl, phenoxy, benzyl, benzyloxy, phenylethyl or phenylethyloxy each of which is optionally substituted in the phenyl moiety once or more than once by identical or different substituents comprising halogen and/or straightchain or branched alkyl having from 1 to 4 carbon atoms and/or straight-chain or branched halogenoalkyl having from 1 to 4 carbon atoms and from 1 to 9 identical or different halogen atoms and/or straight-chain or branched alkoxy having from 1 to 4 carbon atoms and/or straight-chain or branched halogenoalkoxy having from 1 to 4 carbon atoms and 1 to 9 identical or different halogen atoms, Z represents a radical of the formula -O-$R^3$ or -$NR^4R^5$ and n represents a number 0, 1, 2, 3 or 4, where $R^3$ represents straight-chain or branched alkyl having from 1 to 6 carbon atoms and $R^4$ and $R^5$, independently of one another, each represent hydrogen, straight-chain or branched alkyl having from 1 to 8 carbon atoms, straight-chain or branched halogenoalkyl having from 1 to 6 carbon atoms and from 1 to 13 identical or different halogen atoms, or represent straight-chain or branched alkoxy having from 1 to 8 carbon atoms.

Particularly preferred compounds of the formula (IX) are those in which $R^1$ represents straight-chain or branched alkyl having from 1 to 4 carbon atoms or represents straight-chain or branched alkoxy having from 1 to 4 carbon atoms, $R^7$ and $R^8$ are either identical and represent straight-chain or branched alkyl having from 1 to 4 carbon atoms, or together represent a divalent alkylenediyl radical having from 2 to 5 carbon atoms, A represents fluorine, chlorine or bromine or represents aryloxy having 6 or 10 carbon atoms or heteroaryloxy having from 2 to 9 carbon atoms and from 1 to 3 identical or different heteroatoms—in particular nitrogen, oxygen and/or sulphur—each of which is optionally substituted once to five times by identical or different substituents, possible substituents in each case being:

Halogen, cyano, nitro, in each case straight-chain or branched alkyl, alkoxy or alkylthio having in each case from 1 to 4 carbon atoms, in each case straight-chain or branched alkenyl or alkenyloxy having in each case from 2 to 5 carbon atoms, in each case straight-chain or branched alkinyl or alkinyloxy having in each case from 2 to 5 carbon atoms, in each case straight-chain or branched halogenoalkyl, halogenoalkoxy or halogenoalkylthio having in each case from 1 to 4 carbon atoms and from 1 to 9 identical or different halogen atoms, in each case straight-chain or branched halogenoalkenyl or halogenoalkenyl having in each case from 2 to 5 carbon atoms and from 1 to 5 identical or different halogen atoms, in each case straight-chain or branched halogenoalkinyl or halogenoalkinyloxy having in each case from 2 to 5 carbon atoms and from 1 to 5 identical or different halogen atoms, in each case straight-chain or branched alkoxycarbonyl, hydroximinoalkyl or alkoximinoalkyl having in each case from 1 to 4 carbon atoms in the individual alkyl moieties, divalent dioxyalkylene having from 1 to 3 carbon atoms which is optionally substituted once to four times by identical or different substituents comprising halogen and/or straight-chain or branched alkyl having from 1 to 4 carbon atoms and/or straight-chain or branched halogenoalkyl having from 1 to 4 carbon atoms and from 1 to 9 identical or different halogen atoms—in particular fluorine, chlorine and/or bromine—or phenyl, phenoxy, benzyl, benzyloxy, phenylethyl or phenylethyloxy each of which is optionally substituted in the phenyl moiety once to five times by identical or different substituents comprising halogen and/or straight-chain or branched alkyl having from 1 to 4 carbon atoms and/or straight-chain or branched halogenoalkyl having from 1 to 3 carbon atoms and from 1 to 7 identical or different halogen atoms and/or straight-chain or branched alkoxyhaving from 1 to 4 carbon atoms and/or straight-chain or branched halogenoalkoxy having from 1 to 3 carbon atoms and 1 to 7 identical or different halogen atoms, Z represents a radical of the formula -O-$R^3$ or $NR^4R^5$ and n represents a number 0, 1, 2 or 3, where $R^3$ represents straight-chain or branched alkyl having from 1 to 4 carbon atoms and $R^4$ and $R^5$, independently Of one another, each represent hydrogen, straight-chain or branched alkyl having from 1 to 6 carbon atoms, straight-chain or branched halogenoalkyl having from 1 to 4 carbon atoms and from 1 to 9 identical or different halogen atoms, or represent straight-chain or branched alkoxy having from 1 to 6 carbon atoms.

Very particularly preferred compounds of the formula (I) are those in which $R^1$ represents methyl, methoxy, ethyl or ethoxy, $R^7$ and $R^8$ are either identical and represent methyl or ethyl, or together represent an ethane-1,2-diyl radical or propane-1,3-diyl radical each of which is divalent, A represent chlorine or bromine or represents phenoxy which is optionally substituted once to three times by identical or different substituents, possible substituents being:

Fluorine, chlorine, bromine, cyano, nitro, methyl, ethyl, n- or i-propyl, n-, i-, s- or t-butyl, methoxy, ethoxy, n- or i-propoxy, n-, i-, s- or t-butoxy, methylthio, ethylthio, allyl, butenyl, allyloxy, butenyloxy, trifluoromethyl, trifluoro-methoxy, difluoromethoxy, trifluoromethylthio, difluorochloromethylthio, methoxycarbonyl, ethoxycarbonyl, hydroximinomethyl, hydroximinoethyl, methoximinomethyl, methoximinoethyl, ethoximinomethyl, ethoximinoethyl, divalent dioxymethylene or dioxyethylene each of which is optionally substituted once to four times by identical or different substituents comprising fluorine, chlorine, bromine, methyl, ethyl and/or trichloromethyl, or phenyl, phenoxy, benzyl or benzyloxy each of which is optionally substituted once to three times by identical or different substituents comprising fluorine, chlorine, bromine, methyl, ethyl, methoxy, ethoxy, trifluoromethyl and/or trifluoromethoxy, Z represents a radical of the formula -O-$R^3$ or -$NR^4R^5$ and n represents a number 0.1, or 2, where $R^3$ represents methyl or ethyl and $R^4$ and $R^5$, independently of one another, each represent hydrogen, straight-chain or branched alkyl having from 1 to 4 carbon atoms, halogenoalkyl having from 1 to 4 carbon atoms and from 1 to 5 identical or different halogen atoms, or represent straight-chain or branched alkoxy having from 1 to 4 carbon atoms.

Apart from the compounds mentioned in the Preparation Examples, the following individual 2-aryl-2,2-dialkoxy-acetic acid derivatives general formula (IX) may be mentioned:

$$\underset{A}{R_n^1 - \underset{4}{\overset{3\;2}{\bigcirc}} - \overset{OR^7}{\underset{OR^8}{\overset{|}{C}}} - \overset{O}{\overset{\|}{C}} - Z} \quad (IX)$$

| A | $R^1$ | $R^7$ | $R^8$ | n | Z |
|---|---|---|---|---|---|
| Cl | H | $C_2H_5$ | $C_2H_5$ | 0 | $-O-C_2H_5$ |
| Br | H | $C_2H_5$ | $C_2H_5$ | 0 | $-O-C_2H_5$ |
| Cl | H | $CH_3$ | $CH_3$ | 0 | $-NH-CH_3$ |
| Cl | H | $CH_3$ | $CH_3$ | 0 | $-NH-C_2H_5$ |
| Cl | H | $C_2H_5$ | $C_2H_5$ | 0 | $-NH-CH_3$ |
| Br | H | $CH_3$ | $CH_3$ | 0 | $-NH-CH_3$ |
| Br | H | $C_2H_5$ | $C_2H_5$ | 0 | $-NH-CH_3$ |
| Cl | 4-$CH_3$ | $CH_3$ | $CH_3$ | 1 | $-O-CH_3$ |
| Br | 4-$CH_3$ | $CH_3$ | $CH_3$ | 1 | $-O-CH_3$ |
| $-O-C_6H_5$ | H | $C_2H_5$ | $C_2H_5$ | 0 | $-O-C_2H_5$ |
| $-O-\bigcirc-CH_3$ | H | $CH_3$ | $CH_3$ | 0 | $-O-CH_3$ |
| $-O-\bigcirc-CH_3$ | H | $CH_3$ | $CH_3$ | 0 | $-NH-CH_3$ |

Suitable diluents for carrying out the 1st stage of the process according to the invention are inert organic solvents. These include, in particular, aliphatic, alicyclic or aromatic, optionally halogenated, hydrocarbons, for example benzine, benzene, toluene, xylene, chlorobenzene, dichlorobenzene, petroleum ether, hexane, cyclohexane, dichloromethane, chloroform or carbon tetrachloride; ethers such as diethyl ether, diisopropyl ether, dioxane, tetrahydrofuran or ethylene glycol dimethyl or diethyl ether, diethylene glycol dimethyl or diethyl ether; nitriles such as acetonitrile, propionitrile or benzonitrile; amides such as N,N-dimethylformamide, N,N-dimethylacetamide, N-methylformanilide, N-methylpyrrolidone or hexamethylphosphoric triamide. It is also possible simultaneously to use the alcohols or diols of the formula (IIIa) or, respectively, (IIIb), which are suitable as reactants, as diluents in a corresponding excess.

The first stage of the process according to the invention is preferably carried out in the presence of a suitable reaction auxiliary. Suitable such auxiliaries are all conventional dehydrating agents. These include, in particular, ortho esters, for example methyl orthoformate or ethyl ortho-formate, sulphonic acids, for example methanesulphonic acid or p-toluenesulphonic acid, mineral acids such as hydrochloric acid or sulphuric acid, acidic ion exchangers or a molecular sieve. It is also possible to remove from the reaction mixture by azeotropic distillation the water of reaction which is liberated.

When carrying out the first stage of the process according to the invention, the reaction temperatures can be varied within a relatively large range. The temperatures used are in general from 0° C. to +150° C., preferably from 200° C. to +120° C.

The first stage of the process according to the invention is usually carried out under atmospheric pressure.

However, it is also possible to use increased or reduced pressure.

Carrying out the first stage of the process according to the invention involves the use, per mole of 2-oxo-2-phenyl-acetic acid derivative of the formula (II), of in general from 1.0 to 50.0 mol, preferably from 1.0 to 20.0 mol, of alcohol or diol of the formula (IIIa) or, respectively, (IIIb) and optionally from 1.0 to 10.0 mol, preferably from 1.0 to 5.0 mol, of reaction auxiliary. Implementation of the reaction and the working-up and isolation of the reaction products are carried out by commonly known methods (compare also in this respect the Preparation Examples).

Suitable diluents for carrying out the second stage of the process according to the invention are inert organic solvents. These include, in particular, aliphatic, alicyclic or aromatic, optionally halogenated, hydrocarbons, for example benzine, benzene, toluene, xylene, chlorobenzene, dichlorobenzene, petroleum ether, hexane, cyclohexane, dichloromethane, chloroform or carbon tetrachloride; ethers such as diethyl ether, diisopropyl ether, dioxane or tetrahydrofuran or ethylene glycol dimethyl or diethyl ether, diethylene glycol dimethyl or diethyl ether; ketones such as acetone, butanone or methyl isobutyl ketone; nitriles such as acetonitrile, propionitrile or benzonitrile; amides such as N,N-dimethylformamide, N,N-dimethylacetamide, N-methylformanilide, N-methylpyrrolidone or hexamethylphosphoric triamide; esters such as methyl acetate or ethyl acetate; sulphoxides such as dimethyl sulphoxide or sulpholane, or alcohols such as methanol, ethanol, n- or i-propanol, ethylene glycol monomethyl ether, ethylene glycol monoethyl ether, diethylene glycol monomethyl ether or diethylene glycol monoethyl ether.

The 2nd stage of the process according to the invention is preferably carried out in the presence of a suitable reaction auxiliary. Suitable such auxiliaries are all conventional inorganic or organic bases. These include, for example, alkaline earth metal or alkali metal hydrides, hydroxides, amides, alcoholares, acetates, carbonates or hydrogen carbonates, for example sodium hydride, sodium amide, sodium methylate, sodium ethylate, potassium tert-butylate, sodium hydroxide, potassium hydroxide, ammonium hydroxide, sodium acetate, potassium acetate, calcium acetate, ammonium acetate, sodium carbonate, potassium carbonate, potassium hydrogen carbonate, sodium hydrogen carbonate or ammonium carbonate, and tertiary amines such as trimethylamine, triethylamine, tributylamine, N,N-dimethylaniline, pyridine, N-methylpiperidine, N,N-dimethylaminopyridine, diazabicyclooctane (DABCO), diazabicyclononene (DBN) or diazabicycloundecene (DBU).

The second stage of the process according to the invention, moreover, is preferably carried out in the presence of a suitable catalyst. Suitable such catalysts are in particular copper(I) salts, for example copper (I) chloride. In this context, it may be advantageous to add catalytic amounts of a suitable phase-transfer catalyst, for example 15-crown-5, 18-crown-6 or tris-[2-(2-methoxy-ethoxy) -ethyl]-amine.

When carrying out the second stage of the process according to the invention, the reaction temperatures can be varied in a relatively wide range. The temperatures used are in general from 50° C. to +250° C., preferably from 120° C. to +200° C.

The second stage of the process according to the invention is usually carried out under atmospheric pressure. However, it is also possible to work under increased or reduced pressure.

Carrying out the second stage of the process according to the invention involves the use, per mole of 2-aryl-2,2-dialkoxy-acetic acid derivative of the formula (IV), of in general from 1.0 to 1.5 mol, preferably from 1.0 to 1.2 mol, of hydroxy compound of the formula (V), from 1.0 to 1.5 mol, preferably from 1.0 to 1.2 mol, of basic reaction auxiliary and optionally from 0.0001to 1.0 mol, preferably from 0,001 to 0.1 mol, of copper(I) salt catalyst. Implementation of the reaction and the working-up and isolation of the reaction products are carried out in analogy to known methods (compare also in this respect the Preparation Examples ) .

Suitable diluents for carrying out the third stage according to the invention are inert organic solvents, these include, in particular, aliphatic, alicyclic or aromatic, optionally halogenated, hydrocarbons, for example benzine, benzene, toluene, xylene, chlorobenzene, dichlorobenzene, petroleum ether, hexane, cyclohexane, dichloromethane, chloroform or carbon tetrachloride; ethers such as diethyl ether, diisopropyl ether, dioxane or tetrahydrofuran or ethylene glycol dimethyl or diethyl ether; nitriles such as acetonitrile, propionitrile or benzonitrile; amides such as N,N-dimethylformamide, N,N-dimethylacetamide, N-dimethylformanilide, N-methyl-pyrrolidone or hexamethylphosphoric triamide; alcohols such as methanol, ethanol, n- or i-propanol, ethylene glycol monomethyl ether, ethylene glycol monoethyl ether, diethylene glycol monomethyl ether or diethylene glycol monoether ether, and mixtures thereof with water, or pure water.

The 3rd stage of the process according to the invention is preferably carried out in the presence of a suitable reaction auxiliary. Suitable such auxiliaries are all conventional inorganic or organic bases. These include, for example, alkaline earth metal or alkali metal hydrides, hydroxides, amides, alcoholares, acetates, carbonates or hydrogen carbonates, for example sodium hydride, sodium amide, sodium methylate, sodium ethylate, potassium tert-butylate, sodium hydroxide, potassium hydroxide, ammonium hydroxide, sodium acetate, potassium acetate, calcium acetate, ammonium acetate, sodium carbonate, potassium carbonate, potassium hydrogen carbonate, sodium hydrogen carbonate or ammonium carbonate, and tertiary amines such as trimethylamine, triethylamine, tributylamine, N,N-dimethylaniline, pyridine, N-methylpiperidine, N, N-dimethylaminopyridine, diazabicyclooctane (DABCO) , diazabicyclononene (DBN) or diazabicycloundecene (DBU).

When carrying out the 3rd stage of the process according to the invention, the reaction temperatures can be varied in a relatively wide range. The temperatures used are in general from 0° C. to +150° C., preferably from 20° C. to +120° C.

The 3rd stage of the process according to the invention is usually carried out under atmospheric pressure. However, it is also possible to work under increased or reduced pressure.

Carrying out the 3rd stage of the process according to the invention involves the use, per mole of 2-aryl-2,2-dialkoxy-acetic acid derivative of the formula (VI), of in general from 1.0 to 3.0 mol, preferably from 1.0 to 2.0 mol, of hydroxylamine of the formula (VII) or of a corresponding hydrohalide, and optionally from 1.0 to 6.0 mol, preferably from 1.0 to 3.0 mol, of reaction auxiliary. Implementation of the reaction and the working-up and isolation of the reaction products are carried out by known methods.

Suitable diluents for carrying out the 4th stage of the process according to the invention (amidation reaction), which is to be carried out optionally, are inert organic solvents. These include, in particular, aliphatic, alicyclic or aromatic, optionally halogenated, hydrocarbons, for example benzine, benzene, toluene, xylene, chlorobenzene, dichlorobenzene, petroleum ether, hexane, cyclohexane, dichloromethane, chloroform or carbon tetrachloride; ethers such as diethyl ether, diisopropyl ether, dioxane or tetrahydrofuran or ethylene glycol dimethyl or diethyl ether; nitriles such as acetonitrile, propionitrile or benzonitrile; amides such as N,N-dimethylformamide, N,N-dimethylacetamide, N-methyl-formanilide, N-methylpyrrolidone or hexamethylphosphoric triamide; sulphoxides such as dimethyl sulphoxide or sulpholane or alcohols such as methanol, ethanol, n- or i-propanol, ethylene glycol monomethyl ether, ethylene glycol monoethyl ether, diethylene glycol monomethyl ether or diethylene glycol monoethyl ether.

It is also possible simultaneously to use the amine of the formula (VIII), which is used as a reactant, as a diluent, in a corresponding excess.

The 4th stage of the process according to the invention (amidation reaction), which is to be carried out optionally, is preferably carried out in the presence of a suitable reaction auxiliary. Suitable such auxiliaries are all conventional inorganic or organic bases. These include, for example, alkaline earth metal or alkali metal hydrides, hydroxides, amides, alcoholares, acetates, carbonates or hydrogen carbonates, for example sodium hydride, sodium amide, sodium methylate, sodium ethylate, potassium tert-butylate, sodium hydroxide, potassium hydroxide, ammonium hydroxide, sodium acetate, potassium acetate, calcium acetate, ammonium acetate, sodium carbonate, potassium carbonate, potassium hydrogen carbonate, sodium hydrogen carbonate or ammonium carbonate, and tertiary amines such as trimethylamine, triethylamine, tributylamine, N,N-dimethylaniline, pyridine, N-methylpiperidine, N,N-dimethylaminopyridine, diazabicyclooctane (DABCO), diazabicyclononene (DBN) or diazabicycloundecene (DBU).

It is also possible simultaneously to use the amine of the formula (VIII), which is used as a reactant, as a reaction auxiliary, in an appropriate excess.

When carrying out the 4th stage of the process according to invention (amidation reaction), which is to be carried out optionally, the reaction temperatures can be varied in a relatively wide range. The temperatures used are in general from -30° C. to +150° C., preferably from −20° C. to +120° C.

The 4th stage of the process according to the invention (amidation reaction), which is to be carried out optionally, is usually carried out under atmospheric pressure. However, it is also possible to work under increased pressure, for example at between 1 and 100 bar.

Carrying out the 4th stage of the process according to the invention (amidation reaction), which is to be carried out optionally, involves the use, per mole of 2-aryl-2,2-dialkoxy-acetic acid derivatives of the formula (IVa) and (VIa) or per mole of 2-oximinoacetic acid derivative of the formula (Ia), of in general from 1.0 to 3.0 mol, preferably from 1.0 to 1.5 mol, of amine of the formula (VIII), and optionally from 0.1 to 3.0 mol, preferably from 0.5 to 1.5 mol, of base used as reaction auxiliary. If the amidation reaction is interposed between the first and second stages of the process according to the invention, 2-aryl-2,2-dialkoxy-acetic acid derivatives of the formula (IVa) are used as starting compounds; if the amidation reaction is interposed between the 2nd and 3rd stages of the process according to the invention, 2-aryl-2,2-dialkoxy-acetic acid derivatives of the formula (VIa) are used as starting compounds; if the amidation reaction is carried out after carrying out the third stage of the process according to the invention, 2-oximinoacetic acid derivatives of the formula (Ia) are used as starting compounds. Implementation of the reaction and the working-up and isolation of the reaction products are carried out in each case by analogy with known methods.

The products are purified using conventional methods, for example by column chromatography or by recrystallization.

Characterization is effected on the basis of the melting point or, in the case of compounds which do not crystallize, of the refractive index, or by proton nuclear magnetic resonance spectroscopy ($^1$H-NMR).

The compounds of the formula (I) which can be prepared in. accordance with the invention are known fungicides (cf. e.g. EP 398 692 and EP 468 775).

Preparation Examples:

Example IV-1

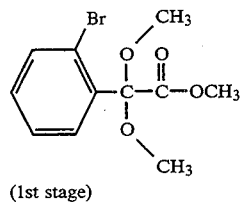

(1st stage)

2 ml of concentrated sulphuric acid are added to 44.8 g (0.226 mol) of methyl 2-bromophenylglyoxylate and 239 g (2.26 mol) of trimethyl orthoformate in 100 ml of methanol, and the mixture is heated at reflux temperature for 24 hours. To work up the reaction mixture it is cooled, 10 ml of saturated sodium hydrogen carbonate solution are added and this mixture is subsequently concentrated in vacuo, and the residue is taken up with ethyl acetate, washed with water, dried over sodium sulphate, concentrated in vacuo and distilled under a high vacuum.

Methyl 2,2-dimethoxy-2-(2-bromophenyl)-acetate (yield 85% of theory; melting point 55° C.) is obtained.

Example VI-I:

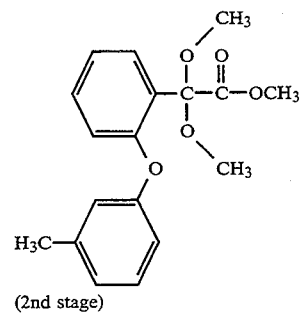

(2nd stage)

10.1 g (0.1 mol) of 3-methylphenol are added to a solution of 5.4 g (0.1 mol) of sodium methylate in 100 ml of methanol, and the mixture is concentrated to dryness. 3.23 g (0.01 mol) of tris-[2-(2-methoxyethoxy)-ethyl]amine, 1 g (0.01 mol) of copper(I) chloride, 60 ml of diethylene glycol dimethyl ether and 28.9 g (0.1 mol) of methyl 2,2-dimethoxy-2-(2-bromophenyl)-acetate are added to the residue, and the mixture is heated with stirring at 165° C. for 48 hours. To work up the reaction mixture, it is cooled, water is added, the mixture is extracted with dichloromethane, the organic phase is dried and concentrated in vacuo and the residue is chromatographed on silica gel (eluent: cyclohexane/ethyl acetate 3:1)

Methyl 2,2-dimethoxy-2-[2-(3-methylphenoxy)-phenyl]acetate is obtained as an oil (yield 75% of theory).

$^1$H-NMR (CDCl$_3$:tetramethylsilane): =2.3 (3H); 3.2 (6H); 3.6 (3H); 6.65–7.9 (5H) ppm.

Example I-11:

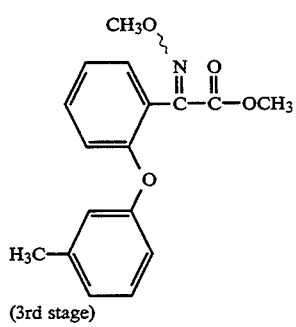

(3rd stage)

1 ml of concentrated hydrochloric acid is added to 3.16 g (0.01 mol) of methyl 2,2-dimethoxy-2-[2-(3-methylphenoxy)-phenyl]-acetate and 1.5 g (0.0175 mol) O-methylhydroxylamine hydrochloride in 100 ml of methanol, and the mixture is heated at reflux temperature for 18 hours. To work up the reaction mixture it is concentrated, the residue is taken up in ethyl acetate, washed with saturated aqueous sodium hydrogen carbonate solution, dried over sodium sulphate and concentrated in vacuo, and the residue is chromatographed on silica gel (eluent: cyclohexane/ethyl acetate 3:1) Methy 2-methoximino -2-[2-(3-methylphenoxy)-phenyl]-acetate is obtained as an oil (yield 70% of theory).

Example I-2:

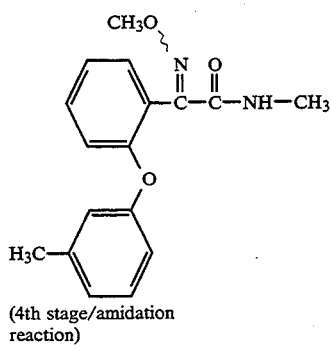

(4th stage/amidation reaction)

Methylamine gas is passed into a solution of 2.99 g (0.01 mol) of methyl 2-methoximino-2-[2-(3-methyl-phenoxy)-phenyl]-acetate in 200 ml of ethanol with ice cooling until saturation is reached, and the reaction mixture is subsequently stirred at 20° C. for 18 hours. To work up the mixture it is concentrated and the residue is recrystallized from ethanol.

2-Methoximino-(N-methyl)-2-[2-(3-methylphenoxy)-phenyl]acetamide (yield 70% of theory).

In a corresponding manner, and in accordance with the general indications for the preparation, the following 2-aryl-2,2-dialkoxy-acetic acid derivatives of the general formula (IX) are obtained:

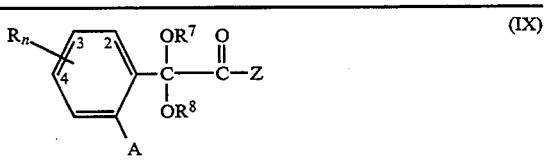

| Ex. No. | A | R$^1$ | R$^7$ | R$^8$ | n | Z | physical properties |
|---|---|---|---|---|---|---|---|
| IV-2 | Cl | H | CH$_3$ | CH$_3$ | 0 | —O—CH$_3$ | m.p. 73–76° C. |
| VI-2 | ⌬—O— | H | CH$_3$ | CH$_3$ | 1 | —O—CH$_3$ | $^1$H-NMR*): 3.2 |

*)The $^1$H-NMR spectra were recorded in deuterochloroform (CDCl$_3$) with tetramethylsilane (TMS) as internal standard. The value given is the chemical shift δ in ppm.

We claim:
1. Process for the preparation of 2-oximinoacetic acid derivatives of the general formula (I)

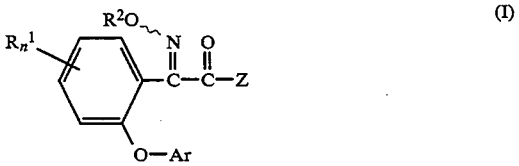

in which
R$^1$ represents alkyl or alkoxy,
R$^2$ represents alkyl,
Ar represents optionally substituted aryl or heteroaryl,
represents a radical of the formula -O-R$^3$ or -NR$^4$R$^5$ and
n represents a number 0, 1, 2, 3 or 4, where
R$^3$ represents alkyl and $R^4$ and $R^5$ independently of one another each represent hydrogen, alkyl, halogenoalkyl or alkoxy, characterized in that 2-oxo-2-phenyl-acetic acid derivatives of the formula (II)

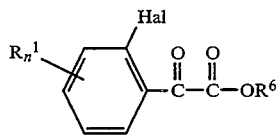

(II)

in which
Hal represents halogen,
$R^6$ represents hydrogen or alkyl and
$R^1$ and n have the meaning given above,
are initially reacted, in a 1st stage, with alcohols of the formula (IIIa)

in which
$R^7$ represents alkyl,
or with diols of the formula (IIIb),

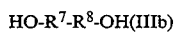

in which
$R^7$ and $R^8$ together represent a divalent alkanediyl, optionally in the presence of a diluent and optionally in the presence of a reaction auxiliary, and, in a subsequent 2nd stage, the 2-aryl-2,2-dialkoxyacetic acid derivatives of the formula (IVa)

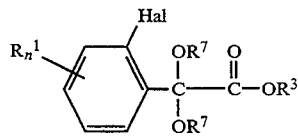

(IVa-1)

and

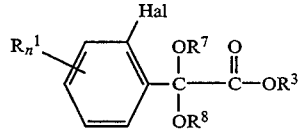

(IVa-2)

in which
$R^1$, $R^3$, $R^7$, $R^8$, Hal and n have the meaning given above,
which compounds are thus obtainable, are reacted with hydroxy compounds of the formula (V)

in which
Ar has the meaning given above,
optionally in the presence of a diluent and optionally in the presence of a reaction auxiliary, and subsequently the 2-aryl-2,2-dialkoxy-acetic acid derivatives of the formula (VIa)

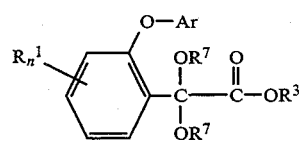

(VIa-1)

and

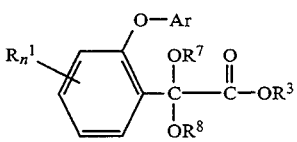

(VIa-2)

in which
$R^1$, $R^3$, $R^7$, $R^8$, Ar and n have the meaning given above,
which compounds are thus obtainable, are reacted in a subsequent 3rd stage with hydroxylamine derivatives of the formula (VII)

in which
$R^2$ has the meaning given above
or with their hydrohalide salts, optionally in the presence of a diluent and optionally in the presence of a reaction auxiliary, to give the 2-oximinoacetic acid derivatives of the formula (Ia)

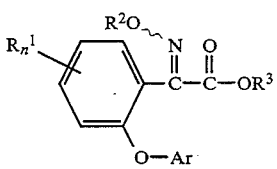

(Ia)

in which
$R^1$, $R^2$, $R^3$, Ar and n have the meaning given above,
where the 2-aryl-2,2-dialkoxy-acetic acid derivatives of the formula (IVa) which are obtainable in the first stage or the 2-aryl-2,2-dialkoxy-acetic acid derivatives of the formula (VIa) which are obtainable in the second stage or the 2-oximinoacetic acid derivatives of the formula (Ia) which are obtainable in the third stage are reacted, optionally in an interposed reaction or in a subsequent reaction, in each case with amines of the formula (VIII)

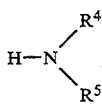

(VIII)

in which
$R^5$ and $R^6$ have the meaning given above,
optionally in the presence of a diluent and optionally in the presence of a reaction auxiliary.

2. Process according to claim 1, in which
$R^1$ represents straight-chain or branched alkyl having from 1 to 6 carbon atoms or represents straight-chain or branched alkoxy having from 1 to 6 carbon atoms,
$R^2$ represents straight—chain or branched alkyl having from 1 to 6 carbon atoms,
Ar represents aryl having from 6 to 10 carbon atoms or heteroaryl having from 2 to 9 carbon atoms and from 1 to 4 identical or different hetero atoms—in particular nitrogen, oxygen and/or sulphur—each of which is optionally substituted once or more than once by identical or different substituents, possible substituents in each case being:

Halogen, cyano, nitro, in each case straight-chain chain or branched alkyl, alkoxy or alkylthio having in each case from 1 to 6 carbon atoms, in each case straight-chain or branched alkenyl or alkenyloxy having in each case from 2 to 6 carbon atoms, in each case straight-chain or branched alkinyl or alkinyloxy having in each case from 2 to 6 carbon atoms, in each case straight-chain or branched halogenoalkyl, halogenoalkoxy or halo-genoalkylthio having in each case from 1 to 6 carbon atoms and from 1 to 13 identical or different halogen atoms, in each case straight-chain or branched halogenoalkenyl or halogenoalkenyloxy having in each case from 2 to 6 carbon atoms and from 1 to 13 identical or different halogen atoms, in each case straight-chain or branched halogenoalkinyl or halogenoalkinyloxy having in each case from 2 to 6 carbon atoms and from 1 to 13 identical or different halogen atoms, in each case straight-chain or branched alkoxycarbonyl, hydroximinoalkyl or alkoximinoalkyl having in each case from 1 to 6 carbon atoms in the individual alkyl moieties, divalent dioxyalkylene having from 1 to 5 carbon atoms which is optionally substituted once or more than once by identical or different substituents comprising halogen and/or straight-chain or branched alkyl having from 1 to 6 carbon atoms and/or straight-chain or branched halogenoalkyl having from 1 to 6 carbon atoms and from 1 to 13 identical or different halogen atoms—in particular fluorine, chlorine, bromine and/or iodine—or phenyl, phenoxy, benzyl, benzyloxy, phenylethyl or phenylethyloxy each of which is optionally substituted in the phenyl moiety once or more than once by identical or different substituents comprising halogen and/or straight-chain or branched alkyl having from 1 to 4 carbon atoms and/or straight-chain or branched halogenoalkyl having from 1 to 4 carbon atoms and from 1 to 9 identical or different halogen atoms and/or straight-chain or branched alkoxy having from 1 to 4 carbon atoms and/or straight-chain or branched halogenoalkoxy having from 1 to 4 carbon atoms and 1 to 9 identical or different halogen atoms, Z represents a radical of the formula $-O-R^3$ or $-NR^4R^5$ and n represents a number 0, 1, 2, 3 or 4, where $R^3$ represents straight-chain or branched alkyl having from 1 to 6 carbon atoms and $R^4$ and $R^5$, independently of one another, each represent hydrogen, straight-chain or branched alkyl having from 1 to 8 carbon atoms, straight-chain or branched halogenoalkyl having from 1 to 6 carbon atoms and from 1 to 13 identical or different halogen atoms, or represent straight-chain or branched alkoxy having from 1 to 8 carbon atoms.

3. Process according to claim 1, in which $R^1$ represents straight-chain or branched alkyl having from 1 to 4 carbon atoms or represents straight-chain or branched alkoxy having from 1 to 4 carbon atoms, $R^2$ represents straight-chain or branched alkyl having from 1 to 4 carbon atoms, Ar represents aryl having 6 or 10 carbon atoms or heteroaryl having from 2 to 9 carbon atoms and from 1 to 3 identical or different hetero atoms—in particular nitrogen, oxygen and/or sulphur—each of which is optionally substituted once to five times by identical or different substituents, possible substituents in each case being:

Halogen, cyano, nitro, in each case straight-chain or branched alkyl, alkoxy or alkylthio having in each case from 1 to 4 carbon atoms, in each case straight-chain or branched alkenyl or alkenyloxy having in each case from 2 to 5 carbon atoms, in each case straight-chain or branched alkinyl or alkinyloxy having in each case from 2 to 5 carbon atoms, in each case straight-chain or branched halogenoalkyl, halogenoalkoxy or halogenoalkylthio having in each case from 1 to 4 carbon atoms and from 1 to 9 identical or different halogen atoms, in each case straight-chain or branched halogenoalkenyl or halogenoalkenyloxy having in each case from 2 to 5 carbon atoms and from 1 to 5 identical or different halogen atoms, in each case straight-chain or branched halogenoalkinyl or halogenoalkinyloxy having in each case from 2 to 5 carbon atoms and from 1 to 5 identical or different halogen atoms, in each case straight-chain or branched alkoxycarbonyl, hydroximinoalkyl or alkoximinoalkyl having in each case from 1 to 4 carbon atoms in the individual alkyl moieties, divalent dioxyalkylene having from 1 to 3 carbon atoms which is optionally substituted once to four times by identical or different substituents comprising halogen and/or straight-chain or branched alkyl having from 1 to 4 carbon atoms and/or straight-chain or branched halogenoalkyl having from 1 to 4 carbon atoms and from 1 to 9 identical or different halogen atoms—in particular fluorine, chlorine and/or bromine—or phenyl, phenoxy, benzyl, benzyloxy, phenylethyl or phenylethyloxy each of which is optionally substituted in the phenyl moiety once to five times by identical or different substituents comprising halogen and/or straight-chain or branched alkyl having from 1 to 4 carbon atoms and/or straight-chain or branched halogenoalkyl having from 1 to 3 carbon atoms and from 1 to 7 identical or different halogen atoms and/or straight-chain or branched alkoxy having from 1 to 4 carbon atoms and/or straight-chain or branched halogenoalkoxy having from 1 to 3 carbon atoms and 1 to 7 identical or different halogen atoms, Z represents a radical of the formula $-O-R^3$ or $NR^4R^5$ and n represents a number 0, 1, 2 or 3, where $R^3$ represents straight-chain or branched alkyl having from 1 to 4 carbon atoms and $R^4$ and $R^5$, independently of one another, each represent hydrogen, straight-chain or branched alkyl having from 1 to 6 carbon atoms, straight-chain or branched halogenoalkyl having from 1 to 4 carbon atoms and from 1 to 9 identical or different halogen atoms, or represent straight-chain or branched alkoxy having from 1 to 6 carbon atoms.

4. Process according to claim 1, in which $R^1$ represents methyl, methoxy, ethyl or ethoxy, $R^2$ represents methyl or ethyl, Ar represents phenyl which is optionally substituted once to three times by identical or different substituents, possible substituents in each case being:

Fluorine, chlorine, bromine, cyano, nitro, methyl, ethyl, n- or i-propyl, n-, i-, s- or t-butyl, methoxy, ethoxy, n- or i-propoxy, n-, i-, s- or t-butoxy, methylthio, ethylthio, allyl, butenyl, allyloxy, butenyloxy, trifluoromethyl, trifluoromethoxy, difluoromethylthio, trifluoro-methylthio, difluoro-chloromethylthio, methoxy-carbonyl, ethoxycarbonyl, hydroximinomethyl, hydroximinoethyl, methoximinomethyl, methoximino-ethyl, ethoximinomethyl, ethoximinoethyl, divalent dioxymethylene or dioxyethylene each of which is optionally substituted once to four times by identical or different substituents comprising fluorine, chlorine, bromine, methyl, ethyl and/or trichloromethyl, or phenyl, phenoxy, benzyl or benzyloxy each of which are optionally substituted once to three times by identical or different substituents comprising fluorine, chlorine, bromine, methyl, ethyl, methoxy, ethoxy, trifluoromethyl and/or trifluoromethoxy, Z represents a radical of the formula $-O-R^3$ or $-NR^4R^5$ and n represents a number 0.1, or 2, where $R^3$ represents methyl or ethyl and $R^4$ and $R^5$, independently of one another, each represent hydrogen, straight-chain or branched alkyl having from 1 to 4 carbon atoms, halogeno-alkyl having from 1 to 4 carbon atoms and from 1 to 5 identical or different halogen atoms, or represent straight-chain or branched alkoxy having from 1 to 4 carbon atoms.

5. 2-Aryl-2,2-dialkoxy-acetic acid derivatives of the formula (IX)

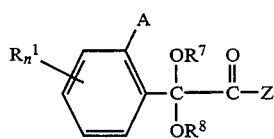

in which $R^1$ represents alkyl or alkoxy, $R^7$ and $R^8$ are either identical and in each case represent alkyl, or together represent a divalent alkanediyl radical, A represents halogen or represents optionally substituted aryloxy or hetero-aryloxy, Z represents a radical of the formula $-O-R^3$ or $-NR^4R^5$ and represents a number 0, 1, 2, 3 or 4, where $R^3$ represents alkyl and $R^4$ and $R^5$, independently of one another, each represent hydrogen, alkyl, halogenoalkyl or alkoxy.

6. Compounds of the formula (IX) according to claim 5, in which $R^1$ represents straight-chain or branched alkyl having from 1 to 6 carbon atoms or represents straight-chain or branched alkoxy having from 1 to 6 carbon atoms, $R^7$ and $R^8$ are either identical and represent straight-chain or branched alkyl having from 1 to 6 carbon atoms, or together represent a divalent alkanediyl radical having from 1 to 6 carbon atoms, A represents fluorine, chlorine, bromine or iodine or represents aryloxyhaving from 6 to 10 carbon atoms or heteroaryloxy having from 2 to 9 carbon atoms and from 1 to 4 identical or different hereto atoms—in particular nitrogen, oxygen and/or sulphur—each of which is optionally substituted once or more than once by identical or different substituents, possible substituents in each case being:

Halogen, cyano, nitro, in each case straight-chain or branched alkyl, alkoxy or alkylthio having in each case from 1 to 6 carbon atoms, in each case straight-chain or branched alkenyl or alkenyloxy having in each case from 2 to 6 carbon atoms, in each case straight-chain or branched alkinyl or alkinyloxyhaving in each case from 2 to 6 carbon atoms, in each case straight-chain or branched halogenoalkyl, halogenoalkoxy or halogenoalkylthio having in each case from 1 to 6 carbon atoms and from 1 to 13 identical or different halogen atoms, in each case straight-chain or branched halogenoalkenyl or halogenoalkenyloxy having in each case from 2 to 6 carbon atoms and from 1 to 13 identical or different halogen atoms, in each case straight-chain or branched halogenoalkinyl or halogenoalkinyloxy having in each case from 2 to 6 carbon atoms and from 1 to 13 identical or different halogen atoms, in each case straight-chain or branched alkoxycarbonyl, hydroximinoalkyl or alkoximinoalkyl having in each case from 1 to 6 carbon atoms in the individual alkyl moieties, divalent dioxyalkylene having from 1 to 5 carbon atoms which is optionally substituted once or more than once by identical or different substituents comprising halogen and/or straight-chain or branched alkyl having from 1 to 6 carbon atoms and/or straight-chain or branched halogenoalkyl having from 1 to 6 carbon atoms and from 1 to 13 identical or different halogen atoms—in particular fluorine, chlorine, bromine and/or iodine—or phenyl, phenox y, benzyl, benzyloxy, phenylethyl or phenylethyloxy each of which is optionally substituted in the phenyl moiety once or more than once by identical or different substituents comprising halogen and/or straight-chain or branched alkyl having from 1 to 4 carbon atoms and/or straight-chain or branched halogenoalkyl having from 1 to 4 carbon atoms and from 1 to 9 identical or different halogen atoms and/or straight-chain or branched alkoxy having from 1 to 4 carbon atoms and/or straight-chain or branched halogenoalkoxyhaving from 1 to 4 carbon atoms and 1 to 9 identical or different halogen atoms, Z represents a radical of the formula $-O-R^3$ or $-NR^4R^5$ and n represents a number 0, 1, 2, 3 or 4, where $R^3$ represents straight-chain or branched alkyl having from 1 to 6 carbon atoms and $R^4$ and $R^5$, independently of one another, each represent hydrogen, straight-chain or branched alkyl having from 1 to 8 carbon atoms, straight-chain or branched halogenoalkyl having from 1 to 6 carbon atoms and from 1 to 13 identical or different halogen atoms, or represent straight-chain or branched alkoxy having from 1 to 8 carbon atoms.

7. Use of the compounds of the formula (IX) in which $R^1$ represents alkyl or alkoxy, $R^7$ and $R^8$ are either identical and in each case represent alkyl, or together represent a divalent alkanediyl radical, A represents haloqen or represent optionally substituted aryloxy or heteroaryloxy, Z represents a radical of the formula $-O-R^3$ or $-NR^4R^5$ and represents a number 0, 1, 2, 3, or 4, where $R^3$ represents alkyl and $R^4$ and $R^5$, independent of one another each represent hydrogen, alkyl, halogenoalkyl or alkoxy for the preparation of 2-oximinoacetic acid derivatives of the formula (I) according to claim 1.

* * * * *